United States Patent
Saito et al.

(10) Patent No.: US 7,352,461 B2
(45) Date of Patent: Apr. 1, 2008

(54) PARTICLE DETECTING METHOD AND STORAGE MEDIUM STORING PROGRAM FOR IMPLEMENTING THE METHOD

(75) Inventors: Susumu Saito, Nirasaki (JP); Hisashi Isozaki, Hasuda (JP); Takashi Kakinuma, Edogawa-ku (JP); Noritaka Nishioka, Toda (JP); Akira Noda, Kounosu (JP)

(73) Assignees: Tokyo Electron Limited, Tokyo (JP); Kabushiki Kaisha TOPCON, Tokyo (JP)

( * ) Notice: Subject to any disclaimer, the term of this patent is extended or adjusted under 35 U.S.C. 154(b) by 283 days.

(21) Appl. No.: 11/289,688

(22) Filed: Nov. 30, 2005

(65) Prior Publication Data

US 2006/0132771 A1    Jun. 22, 2006

Related U.S. Application Data

(60) Provisional application No. 60/636,486, filed on Dec. 17, 2004.

(30) Foreign Application Priority Data

Nov. 30, 2004 (JP) ............................. 2004-347000

(51) Int. Cl.
  *G01N 15/02* (2006.01)
  *G01N 21/00* (2006.01)
(52) U.S. Cl. ................. 356/337; 356/335; 356/338
(58) Field of Classification Search ........ 356/335–343, 356/432–444
  See application file for complete search history.

(56) References Cited

U.S. PATENT DOCUMENTS 3,696,678 A * 10/1972 Mossey ..................... 374/104
4,839,529 A * 6/1989 Fruengel .................... 250/574
4,906,094 A * 3/1990 Ashida ....................... 356/336
5,451,787 A * 9/1995 Taylor ..................... 250/338.5
5,701,172 A * 12/1997 Azzazy ....................... 356/28
5,815,265 A * 9/1998 Molter et al. ............... 356/338
6,794,671 B2 * 9/2004 Nicoli et al. ................ 250/574
7,075,647 B2 * 7/2006 Christodoulou ............. 356/339
2003/0193338 A1 * 10/2003 Krasnobaev et al. ........ 324/464

FOREIGN PATENT DOCUMENTS

JP    2000-146819    5/2000

\* cited by examiner

*Primary Examiner*—Layla G. Lauchman
*Assistant Examiner*—Jarreas Underwood
(74) *Attorney, Agent, or Firm*—Oblon, Spivak, McClelland, Maier & Neustadt, P.C.

(57) ABSTRACT

A particle detecting method which is capable of detecting the number of low-speed particles accurately, and a storage medium storing a program for implementing the method. Intensity of scattered light generated when a light emitted into a gas stream is scattered by a particle is measured using a light receiving sensor at predetermined time intervals. A measuring time period for measuring the scattered light intensity is divided into measurement periods each defined as a predetermined time period, and a measured time point in each measurement period is selected at which a maximum value of the scattered light intensity measured is measured. The number of particles having passed by in front of the light receiving sensor is counted based on the measured time point selected in each measurement period.

8 Claims, 7 Drawing Sheets

US 7,352,461 B2

PARTICLE DETECTING METHOD AND STORAGE MEDIUM STORING PROGRAM FOR IMPLEMENTING THE METHOD

BACKGROUND OF THE INVENTION

1. Field of the Invention

The present invention relates to a particle detecting method and a storage medium storing a program for implementing the method, and more particularly to a particle detecting method of detecting the number of particles carried by a gas stream.

2. Description of the Related Art

In general, in a substrate processing apparatus having a processing chamber in which desired processing is carried out on a semiconductor wafer (hereinafter referred to as "the wafer") as a substrate using a process gas, particles, such as metal particles of aluminum, are produced due to contact between the wafer and a mounting stage on which the wafer is placed, and reaction products, such as fluorocarbon polymer particles, are produced due to reaction of the process gas.

These particles are deposited on the wafer, causing degradation of the quality of a semiconductor device formed on a surface of the wafer. To avoid this problem, in the substrate processing apparatus, the particle diameters and number of particles within the processing chamber are detected so as to maintain the particle diameters and the particle count below respective predetermined values. When the particle diameters and the particle count become larger than the respective predetermined values, operation of the substrate processing apparatus is stopped for cleaning of the processing chamber and replacement of component parts.

As a method of detecting particles of the above-mentioned kinds, a method has conventionally been known in which scattered light generated due to the presence of particles is measured by a particle monitor provided in an intermediate portion of a purged gas flow path through which particles and gases are evacuated from the processing chamber.

In this method in which scattered light is measured, a light beam (light flux) formed in a sheet shape (belt shape) is passed through a gas stream flowing through the purged gas flow path, and the intensity of a scattered light generated when a particle contained in the gas stream passes through the light beam is measured by a sensor disposed in facing relation to the purged gas flow path, whereafter the particle diameter of the particle is calculated based on the measured scattered light intensity (see e.g. Japanese Laid-Open Patent Publication (Kokai) No. 2000-146819).

Particles each pass by in front of the sensor as time elapses. For this reason, as indicated by the values of scattered light intensity associated with respective particles Pf and Ps shown in FIG. 7, scattered light intensity measured by the sensor progressively increases with the lapse of time at first, and then progressively decreases after having reached its extreme value. To detect the particle diameter of each particle accurately, it is preferred that associated scattered light intensity is continuously measured with the lapse of time. In this case, however, the amount of measurement data becomes immense, and therefore it inevitably takes a long time to process the data. Further, changes in scattered light intensity may be approximated using the Gaussian curve based on a plurality of pieces of measurement data, but also in this case, curve fitting requires time.

To solve this problem, in recent years, a detection method has been employed in which a measuring time period is divided into measurement periods each defined by a predetermined time period, and the scattered light intensity is measured (discretely) at predetermined time intervals in the measurement periods (T1 to T5 in FIG. 7). In this detection method, during each measurement period, the maximum value of scattered light intensity during the measurement period is selected, and stored in a memory or the like. Further, if the selected maximum value of scattered light intensity exceeds a predetermined threshold value, it is determined that a single particle is passing, and the particle diameter of the particle having passed is calculated based on the maximum value of scattered light intensity. According to this detection method, since only one maximum value of scattered light intensity is selected and stored during each measurement period, it is possible to reduce the amount of data, thereby shortening a time period required for data processing.

Further, according to this detection method, insofar as a particle, such as the particle Pf in FIG. 7, which passes by in front of the sensor within a single predetermined period (T1) is concerned, only one maximum value of scattered light intensity PfI is selected, so that it is possible to accurately measure the number of particles having passed by in front of the sensor.

In the above described detection method, however, insofar as a particle, such as a particle Ps in FIG. 7, which passes by in front of the sensor over a plurality of predetermined periods (T2 to T5), i.e. a low-speed particle is concerned, four maximum values $PfI_1$ to $PfI_4$ of scattered light intensity in the respective associated periods T2 to T5 are selected, and therefore even though the single particle Ps has passed by in front of the sensor in actuality, it is erroneously determined that four particles at the maximum have passed by in front of the sensor. In short, the number of low-speed particles cannot be detected accurately.

If the number of particles cannot be detected accurately, unnecessary cleaning of the processing chamber or unnecessary replacement of component parts might be performed, resulting in degradation of the operating efficiency of the substrate processing apparatus.

SUMMARY OF THE INVENTION

It is an object of the present invention to provide a particle detecting method which is capable of detecting the number of low-speed particles accurately, and a storage medium storing a program for implementing the method.

To attain the above object, in a first aspect of the present invention, there is provided a particle detecting method of detecting particles carried by a gas stream, comprising a scattered light intensity-measuring step of measuring intensity of scattered light generated when a light emitted into the gas stream is scattered by a particle, using a light receiving unit at predetermined time intervals, a maximum intensity measuring timing-selecting step of dividing a measuring time period for measuring the scattered light intensity into measurement periods each defined as a predetermined time period, and selecting a measured time point in each measurement period at which a maximum value of the scattered light intensity measured is measured, and a passed particle counting step of counting a number of particles having passed by in front of the light receiving unit, based on the measured time point selected in each measurement period.

With the configuration of the first aspect of the present invention, the number of particles having passed by in front of the light receiving unit is counted based on measured time points at each of which the maximum value of the scattered light intensity in each measurement period is measured, so that it is possible to prevent the number of particles from being counted only based on respective values of scattered light intensity measured in the measurement periods. Therefore, the number of low-speed particles which pass by in front of the light receiving unit over a plurality of measurement periods can be accurately detected.

Preferably, the passed particle counting step determines that the particle has not passed by in front of the light receiving unit, when the measured time point selected in the measurement period corresponds to either a beginning or an end of the measurement period.

With the configuration of this preferred embodiment, when a measured time point at which the maximum value of scattered light intensity is measured in an associated measurement period corresponds to either the beginning or the end of the measurement period, it is determined that no particle has passed by in front of the light receiving unit, so that the number of low-speed particles each of which passes by in front of the light receiving unit over a plurality of measurement periods can be accurately detected.

Preferably, the scattered light intensity-measuring step does not measure scattered light intensity below a threshold value.

With the configuration of this preferred embodiment, since scattered light intensity lower than the predetermined threshold value is not measured, it is possible to avoid measuring the intensity of light other than scattered light generated due to the presence of a particle, thereby detecting the number of particles more accurately.

Preferably, the maximum intensity measuring timing-selecting step selects not only the measured time point, but also the maximum value of scattered light intensity associated with the measured time point.

With the configuration of this preferred embodiment, not only the measured time point at which the maximum value of scattered light intensity is measured but also the maximum value of scattered light intensity is selected, which makes it easy to associate the time point with the maximum value of scattered light intensity.

Preferably, the particle detecting method further comprises a particle diameter calculating step of calculating particle diameters of the respective particles based on the maximum values of the scattered light intensity measured in the measurement periods.

With the configuration of this preferred embodiment, since the particle diameter of a particle is calculated based on the associated maximum value of scattered light intensity, it is possible to accurately calculate the size of the particle having passed by in front of the light receiving unit.

Preferably, the scattered light intensity-measuring step measures the scattered light intensity of the light emitted into the gas stream in a processing chamber provided in a substrate processing apparatus.

With the configuration of this preferred embodiment, the intensity of scattered light from the light emitted through the gas stream within the processing chamber of the substrate processing apparatus is measured. Therefore, the number of particles within the processing chamber, which cause degradation of the quality of a semiconductor device, can be directly detected, which makes it possible to reliably prevent the quality of the semiconductor device from being degraded.

Preferably, the scattered light intensity-measuring step measures the scattered light intensity of the light emitted into the gas stream in a purged gas flow path connected to a processing chamber provided in a substrate processing apparatus.

With the configuration of this preferred embodiment, the intensity of scattered light from the light emitted through the gas stream within the purged gas flow path connected to the processing chamber of the substrate processing apparatus is measured. In the substrate processing apparatus, particles within the processing chamber are purged through the purged gas flow path prior to decompression of the processing chamber. Therefore, particles can be easily detected.

To attain the above object, in a second aspect of the present invention, there is provided a computer-readable storage medium storing a particle detecting program for causing a computer to execute a particle detecting method of detecting particles carried by a gas stream, the program comprising a scattered light intensity-measuring module for measuring intensity of scattered light generated when a light emitted into the gas stream is scattered by a particle, using a light receiving unit at predetermined time intervals, a maximum intensity measuring timing-selecting module for dividing a measuring time period for measuring the scattered light intensity into measurement periods each defined as a predetermined time period, and selecting a measured time point in each measurement period at which a maximum value of the scattered light intensity measured is measured, and a passed particle counting module counting a number of particles having passed by in front of the light receiving unit, based on the measured time point selected in each measurement period.

The above and other objects, features, and advantages of the invention will become more apparent from the following detailed description taken in conjunction with the accompanying drawings.

BRIEF DESCRIPTION OF THE DRAWINGS

FIGS. 6A to 6C are plan views schematically showing the arrangements of respective substrate processing systems each including a plurality of substrate processing apparatuses to which is applied the particle detecting method according to the present embodiment, and at least one conveying chamber, in which:

FIG. 6A shows a cluster-type substrate processing system;

FIG. 6B shows a parallel-type substrate processing system; and

FIG. 6C shows a substrate processing system having a double arm-type transfer arm.

DETAILED DESCRIPTION OF THE PREFERRED EMBODIMENTS

The present invention will now be described in detail with reference to the drawings showing a preferred embodiment thereof.

First of all, a description will be given of a substrate processing apparatus to which is applied a particle detecting method according to the present embodiment.

Figure 1:
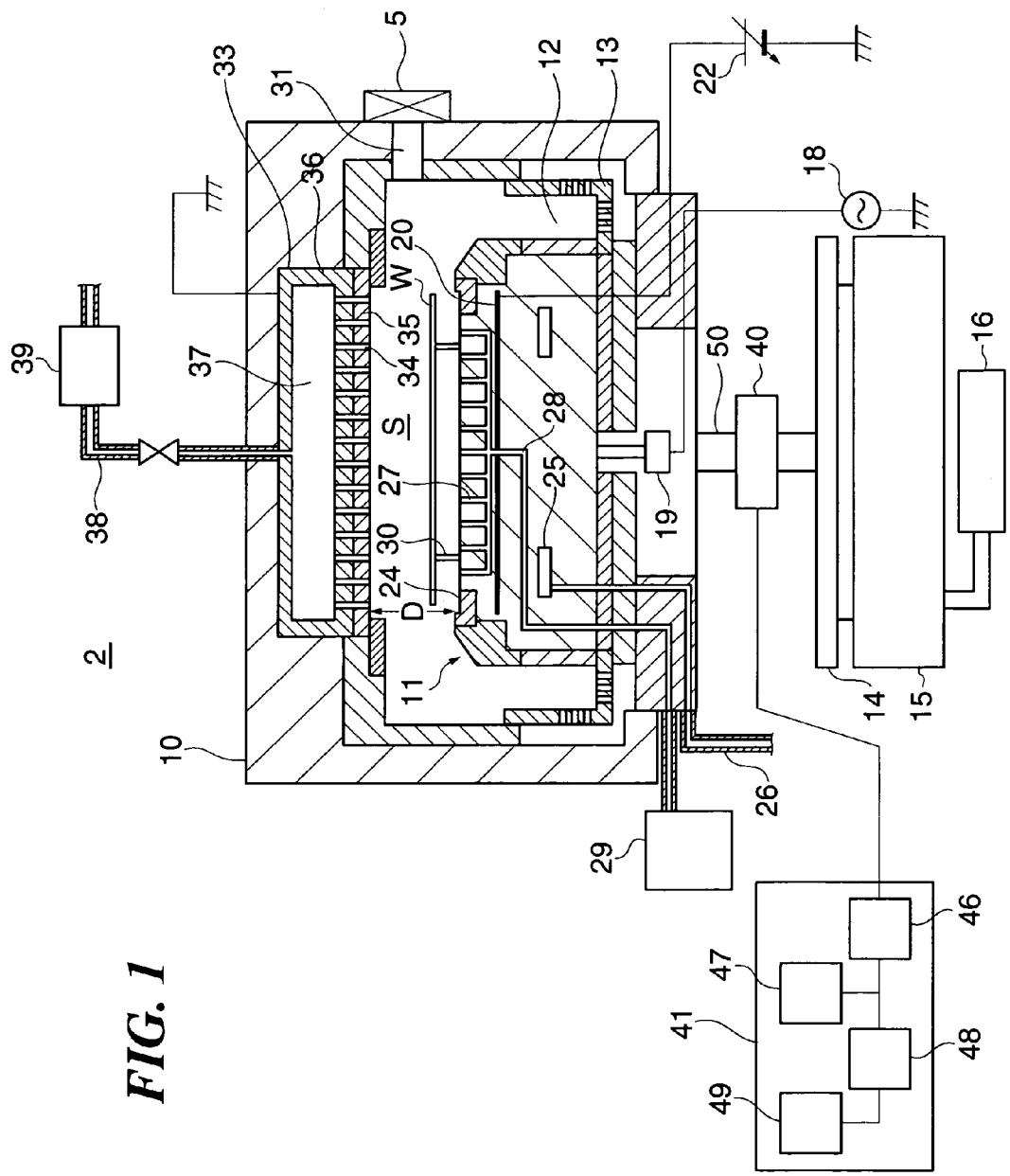
FIG. 1 is a cross-sectional view schematically showing the arrangement of a substrate processing apparatus to which is applied a particle detecting method according to an embodiment of the present invention.

FIG. 1 is a cross-sectional view schematically showing the arrangement of the substrate processing apparatus.

As shown in FIG. 1, the substrate processing apparatus 2, as an etching apparatus for carrying out etching on semiconductor wafers W, has a hollow cylindrical chamber 10 formed of metal such as aluminum or stainless steel. In the chamber 10, there is provided a cylindrical susceptor 11 as a stage on which is placed a semiconductor wafer W having a diameter e.g. of 300 mm.

Between the side wall of the chamber 10 and the susceptor 11, there is formed an evacuation passage 12 functioning as a flow path for discharging gases above the susceptor 11 out of the chamber 10. An annular exhaust plate (partitioning plate) 13 is disposed in an intermediate portion of the evacuation passage 12, and a space of the evacuation passage 12 downstream of the exhaust plate 13 is in communication with an adaptive pressure control (hereinafter referred to as "the APC") valve 14 implemented by a variable butterfly valve, via an evacuation pipe 50 with a diameter of e.g. 150 mm. The APC valve 14 is connected to a turbo-molecular pump (hereinafter referred to as "the TMP") 15 as an evacuation pump for use in vacuuming operation. Further, the APC valve 14 is connected to a dry pump (hereinafter referred to as "the DP") 16 as an evacuation pump via the TMP 15. A purged gas flow path formed by the evacuation pipe 50, the APC valve 14, the TMP 15, and the DP 16 is hereinafter referred to as "the main evacuation line". The main evacuation line not only controls pressure in the chamber 10 using the APC valve 14, but also purges gases and particles from the chamber 10 using the TMP 15 and the DP 16, and further decompresses the chamber 10 to an extent close to vacuum. The evacuation pipe 50 extending between the evacuation passage 12 and the APC valve 14 in the main evacuation line is provided with a particle monitor 40, and the particle monitor 40 is electrically connected to a particle counter 41.

The particle monitor 40 passes a light flux through a purged gas stream flowing through the evacuation pipe 50, to measure the intensity of scattered light generated when particles contained in the gas stream pass through the light flux, and sends the measured scattered light intensity to the particle counter 41. The particle counter 41 determines the particle diameters and number of particles P passing by in front of a light receiving sensor 44, referred to hereinafter, based on the received scattered light intensity, using the particle detecting method, described in detail hereinafter.

A high-frequency power supply 18 is connected to the susceptor 11 via a matching device 19. The high-frequency power supply 18 applies a predetermined high-frequency power to the susceptor 11, whereby the susceptor 11 functions as a lower electrode. The matching device 19 reduces reflection of the high-frequency power from the susceptor 11 to thereby maximize the incident efficiency of the high-frequency power to the susceptor 11.

In an upper space within the susceptor 11, there is disposed a disk-shaped electrode plate 20 formed of a conductive film, for attracting the semiconductor wafer W by an electrostatic attractive force. The electrode plate 20 is electrically connected to a DC power source 22. The semiconductor wafer W is attracted to the upper surface of the susceptor 11 to be held thereon by a Coulomb's force or a Johnsen-Rahbek force generated by a DC voltage applied to the electrode plate 20 from the DC power source 22. Further, in an upper part of the susceptor 11, there is fitted an annular focus ring 24 formed e.g. of silicon (Si). The focus ring 24 causes plasma generated above the susceptor 11 to be converged toward the semiconductor wafer W.

Within the susceptor 11, there is formed an annular refrigerant chamber 25 extending circumferentially along the susceptor 11. A coolant, such as a cooling water, at a predetermined temperature, is circulated and supplied to the refrigerant chamber 25 from a chiller unit, not shown, through a pipe 26. The processing temperature of the semiconductor wafer W on the susceptor 11 is controlled by the temperature of the coolant.

A portion of the upper surface of the susceptor 11 to which the semiconductor wafer W is attracted (hereinafter referred to as "the attracting surface") is formed with a plurality of heat-conducting gas supply holes 27 and heat-conducting gas supply grooves, not shown. The heat-conducting gas supply holes 27, etc. are connected to a heat-conducting gas supply pipe 29, via a heat-conducting gas supply pipe 28 provided within the susceptor 11, and the heat-conducting gas supply pipe 29 supplies heat-conducting gas, such as He gas, into a gap between the attracting surface and the underside surface of the semiconductor wafer W. This heat-conducting gas supply section 29 is also capable of drawing a vacuum between the attracting surface and the underside surface of the semiconductor wafer W.

Further, on the attracting surface, there are provided a plurality of pusher pins 30 as lift pins that can project from the upper surface of the susceptor 11. The pusher pins 30 are moved to project from the attracting surface by conversion of the torque of a motor, not shown, into linear motion by a ball screw or the like. When it is necessary to attract the semiconductor wafer W and hold the same on the attracting surface, the pusher pins 30 are received in the susceptor 11. Then, when the etched semiconductor wafer W is to be carried out from the chamber 10, the pusher pins 30 project from the upper surface of the susceptor 11 so as to lift the semiconductor wafer W upward, away from the susceptor 11.

In a ceiling part of the chamber 10, there is provided a shower head 33. The shower head 33 is grounded, so that it functions as a ground electrode.

The shower head 33 has an electrode plate 35 as a lower face formed with numerous gas vents 34, and an electrode holder 36 removably holding the electrode plate 35. Further, within the electrode holder 36, there is formed a buffer chamber 37 to which is connected a process gas-introducing pipe 38 extending from a process gas supply section, not shown. An MFC (Mass Flow Controller) 39 is provided in an intermediate portion of the process gas-introducing pipe 38. The MFC 39 supplies a predetermined gas, such as process gas or $N_2$ gas, to the chamber 10 through the buffer chamber 37. Further, the MFC 39 controls the flow rate of the gas and cooperates with the APC valve 14 to control the pressure within the chamber 10 to a desired value. An inter-electrode distance D between the susceptor 11 and the shower head 33 is set e.g. to a distance not shorter than 35±1 mm.

A gate valve 5 for opening and closing a semiconductor wafer inlet/outlet port 31 is mounted on a side wall of the chamber 10. In the chamber 10 of the substrate processing apparatus 2, the high-frequency power is applied to the susceptor 11 as described above, and in a space S between the susceptor 11 and the shower head 33, the applied high-frequency power generates a high-density plasma from the process gas. Further, the high-density plasma generates ions and radicals.

In the substrate processing apparatus 2, when etching is to be carried out, first, the gate valve 5 is opened, and a wafer W to be processed is carried into the chamber 10 and placed on the susceptor 11. Then, after particles within the chamber 10 are purged through the main evacuation line, the process gas (e.g. a gaseous mixture comprising $C_4F_8$ gas, $O_2$ gas, and Ar gas at a predetermined flow rate ratio) is introduced into the chamber 10 from the shower head 33 at a predetermined flow rate and a predetermined flow rate ratio, and the pressure in the chamber 10 is controlled to a predetermined value by the APC valve 14, etc. Further, a high-frequency power is applied to the susceptor 11 from the high-frequency power supply 18, and a DC voltage is applied to the electrode plate 20 from the DC power source 22, whereby the semiconductor wafer W is attracted onto the susceptor 11. Then, the process gas discharged from the shower head 33 is turned into plasma as described above. The focus ring 24 causes radicals and ions generated from this plasma to converge on the surface of the semiconductor wafer W to thereby etch the surface of the semiconductor wafer W physically or chemically.

Figure 2:
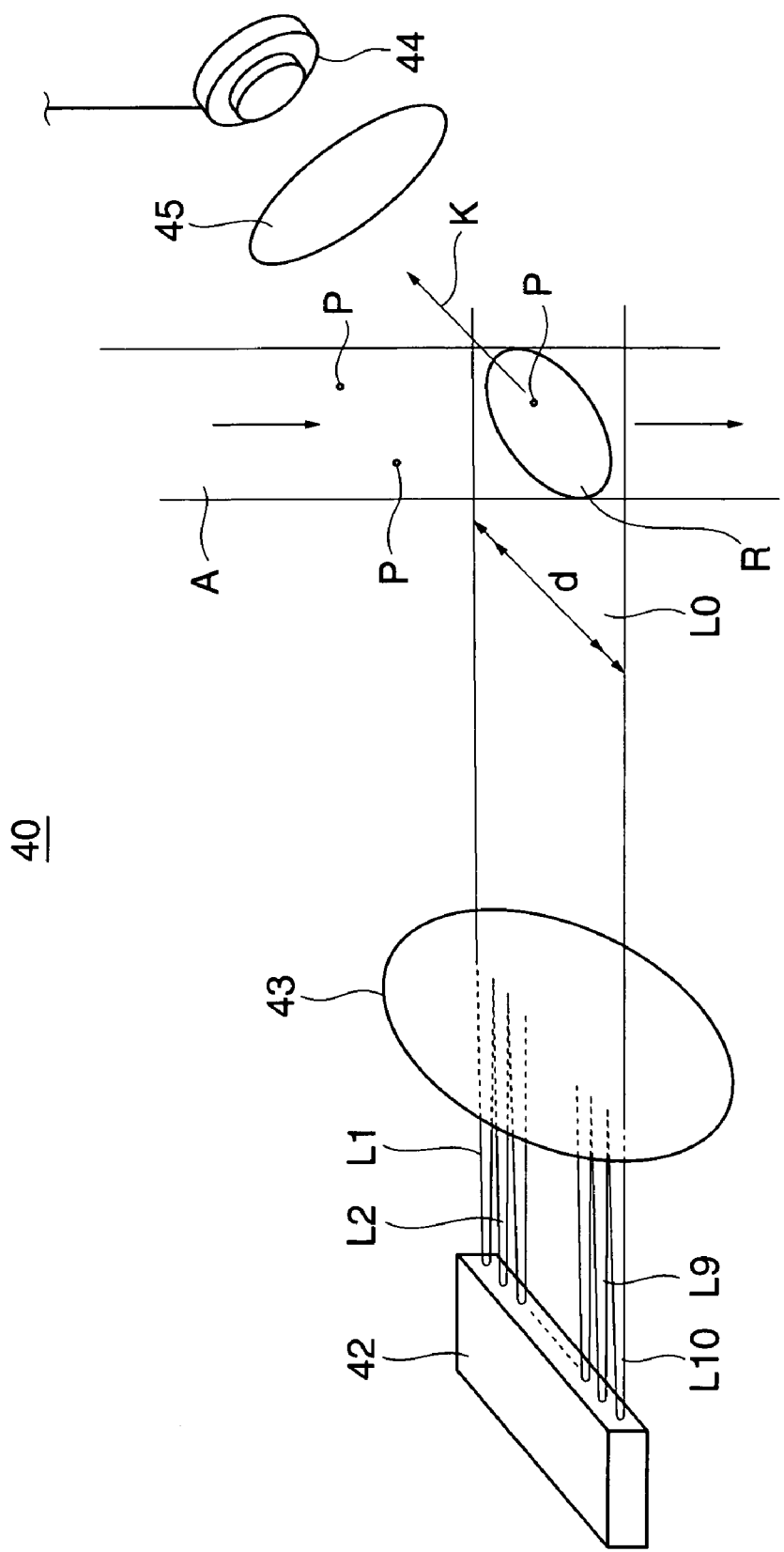
FIG. 2 is a view schematically showing the arrangement of a particle monitor appearing in FIG. 1.

FIG. 2 is a view schematically showing the arrangement of the particle monitor appearing in FIG. 1.

As shown in FIG. 2, the particle monitor 40 is comprised of a laser beam source 42 that emits ten laser beams L1 to L10 arranged in-line, a projection optical system 43 that collects the ten laser beams L1 to L10 emitted in-line from the laser beam source 42 into a single light flux L0 in the form of a belt (whose transverse direction is indicated by "d") and emits the light flux L0 to a purged gas stream A flowing through the evacuation pipe 50 such that the light flux L0 passes through the purged gas stream A while maintaining the transverse direction d thereof in general orthogonal relation to the purged gas stream A, the light receiving sensor 44 that detects light intensity, and an optical detection system 45 that introduces to the light receiving sensor 44 a scattered light K scattered in a direction at a predetermined angle (other than an integral multiple of 180 degrees) with respect to the emitting direction of the light flux L0 when a particle P contained in the purged gas stream A passes through the light flux L0.

The projection optical system 43 causes corresponding ones of the laser beams L1 to L10 emitted from the laser beam source 42 to partly overlap one another, such that the light intensity of the belt-like light flux L0 becomes substantially uniform in distribution in the transverse direction d of the light flux L0 in a purged-gas passage area R where the light flux L0 intersects the purged gas stream A. More specifically, the ten beams L1 to L10 are passed through respective different areas on a single lens forming a part of the projection optical system 43 to thereby convert each of the beams L1 to L10 into a light flux with a small divergent angle, and further, the distance between the laser beam source 42 and the purged-gas passage area R and/or the distance between the single lens and the purged-gas passage area R are/is adjusted, whereby corresponding ones of the beams L1 to L10 are partly superposed one upon another.

Further, the optical detection system 45 is configured to cause the scattered light K generated in the purged-gas passage area R to be converged on the light receiving surface of the light receiving sensor 44. The light receiving sensor 44 measures scattered light intensity of the scattered light K at predetermined time intervals in each of measurement periods each defined as a predetermined time period obtained by dividing a measuring time period for measuring particles P contained in the purged gas stream A, and sends measured values of scattered light intensity and respective associated measured time points at which the scattered light intensity was measured (hereinafter referred to as "time information") as scattered light intensity data to the particle counter 41.

Referring again to FIG. 1, the particle counter 41 is comprised of a maximum scattered light intensity-selecting section 46 that selects the scattered light intensity data of a maximum value of scattered light intensity (hereinafter referred to as "maximum scattered light intensity data": Similarly to the scattered light intensity data, the maximum scattered light intensity data is comprised of a value of scattered light intensity and associated time information) from scattered light intensity data obtained during each measurement period, which are sent from the light receiving sensor 44, a memory 47 that stores the maximum scattered light intensity data, a particle detecting section 48 that calculates the particle diameter of each particle P based on the scattered light intensity contained in the associated maximum scattered light intensity data stored in the memory 47 and counts the number of the particles P, and a display section 49 that displays the particle diameters of particles P and the number of the particles P obtained by the particle detecting section 48.

It is for purposes of ease of association between time information corresponding to a maximum value of scattered light intensity and the maximum value of scattered light intensity itself that the time information corresponding to the maximum value of scattered light intensity and the maximum scattered light intensity are selected together as maximum scattered light intensity data.

The maximum scattered light intensity-selecting section 46 is a computation circuit such as a CPU or an FPGA (Field Programmable Gate Array). The maximum scattered light intensity-selecting section 46 has an internal memory, not shown, for temporarily storing scattered light intensity data obtained during each measurement period and sent from the light receiving sensor 44. When the internal memory stores pieces of scattered light intensity data obtained in a single measurement period, maximum scattered light intensity data is selected from the stored scattered light intensity data. In short, the maximum scattered light intensity-selecting section 46 selects a single piece of maximum scattered light intensity data in each measurement period.

The memory 47 is a writable/erasable storage medium, such as a RAM or an HDD, and stores the maximum scattered light intensity data selected by the maximum scattered light intensity-selecting section 46 in each measurement period. The maximum scattered light intensity-selecting section 46 selects only one piece of maximum scattered light intensity data in each measurement period, and therefore the memory 47 stores a number of pieces of maximum scattered light intensity data which correspond in number to a quotient obtained by dividing the measuring time period by the measurement period.

The particle detecting section 48 is also a computation circuit implemented by a CPU or an FPGA. The particle detecting section 48 calculates the particle diameter of each particle P based on the values of scattered light intensity of the maximum scattered light intensity data stored in the memory 47 and counts the number of the particles P, according to a program and a circuit configuration for implementing the particle detecting method according to the present embodiment.

Although in the above described particle counter 41, the maximum scattered light intensity-selecting section 46 and the particle detecting section 48 are each formed by an independent computation circuit, the two sections 46 and 48 may be formed by a single computation circuit.

Next, a description will be given of the particle detecting method according to the present embodiment.

In the conventional detecting method, the number of particles is detected based on maximum scattered light intensity alone, whereas in the particle detecting method according to the present embodiment, the number of particles is detected based on not only maximum scattered light intensity but also time information. That is, in the present detecting method, the number of particles P having passed by in front of the light receiving sensor 44 is counted based on pieces of time information, as well, which are contained in the maximum scattered light intensity data obtained in respective measurement periods.

Figure 3:
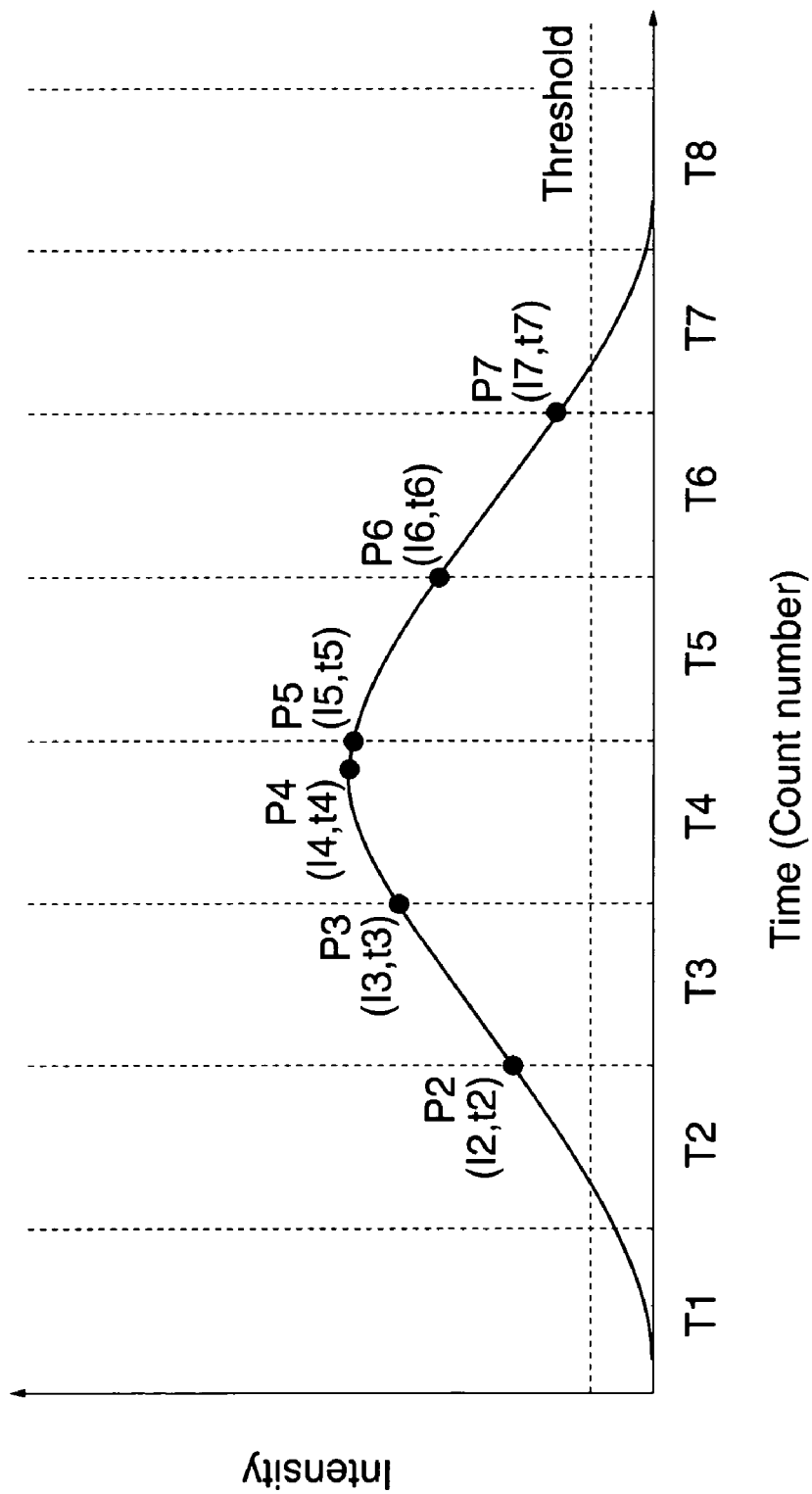
FIG. 3 is a graph showing changes with time in scattered light intensity occurring with a particle having passed by in front of a light receiving sensor over a plurality of measurement periods.

More specifically, in each measurement period, when time information of maximum scattered light intensity data corresponds to either the beginning or the end of the measurement period, it is determined that no particle P has passed by in front of the light receiving sensor 44 in the measurement period. Still more specifically, when scattered light intensity associated with a particle P that passes by in front of the light receiving sensor 44 over a plurality of measurement periods T1 to T8 is measured as shown in FIG. 3, maximum scattered light intensity data Pi obtained in the respective measurement periods T1 (i=1, 2, . . . , 8) (each piece of the data Pi is comprised of scattered light intensity Ii and time information ti) include maximum scattered light intensity data P2 to P7 having scattered light intensity Ii exceeding a predetermined threshold value (threshold in FIG. 3), and time information t2 and t3 of the respective maximum scattered light intensity data P2 and P3 among the maximum scattered light intensity data P2 to P7 correspond to the respective ends of the measurement periods T2 and T3, and therefore it is determined that no particle P has passed by in front of the light receiving sensor 44 in either of the measurement periods T2 and T3. Further, time information t5 to t7 of the maximum scattered light intensity data P5 to P7 correspond to the respective beginnings of the measurement periods T5 to T7, and therefore it is determined that no particle P has passed by in front of the light receiving sensor 44 in any of the measurement periods P5 to P7. On the other hand, in the measurement period T4 associated with the maximum scattered light intensity data P4, time information t4 does not correspond to either the beginning or the end of the measurement period T4, and therefore it is determined that the single particle P has passed by in front of the light receiving sensor 44.

In the present embodiment, the light receiving sensor 44 is disposed in a manner directed toward a central part within the evacuation pipe 50, and therefore a maximum value of scattered light intensity detected by the light receiving sensor 44 is associated with a particle P passing through the central part in the evacuation pipe 50. Therefore, in the present embodiment, the case where it is determined that a particle P has passed by in front of the light receiving sensor 44 means the case where the particle P has passed through the central part in the evacuation pipe 50, whereas the case where it is determined that no particle P has passed by in front of the light receiving sensor 44 includes the case where a particle P has passed through an area other than the central part within the evacuation pipe 50.

In the present embodiment, when scattered light intensity is measured 96 times in each measurement period, by way of example, and assuming that measured time points correspond to respective counts started from 0. Thus, if the time information ti corresponds to a count 0 or a count 95, it is determined that no particle P has passed by in front of the light receiving sensor 44 in the measurement period concerned. In the present example, pieces of time information t2 and t3 correspond to the count 95, and pieces of time information t5 to t7 correspond to the count 0. Therefore, in the measurement periods T2, T3, and T5 to T7, it is determined that no particle P has passed by in front of the light receiving sensor 44. On the other hand, in the measurement period T4 corresponding to the maximum scattered light intensity data P4 which does not correspond to either the count 0 or the count 95, it is determined that a particle P has passed by in front of the light receiving sensor 44.

Thus, the number of particles P having passed by in front of the light receiving sensor 44 over a plurality of measurement periods can be accurately counted.

Although in the above described embodiment, when a piece of time information corresponds to the count 0 or the count 95, it is determined that no particle P has passed by in front of the light receiving sensor 44 in the measurement period concerned, counts that can be used for the determination are not limited to 0 and 95. For example, a predetermined range of counts may be set for use in the determination in consideration of influence of noise or the like of light received by the light receiving sensor 44. More specifically, when time information corresponds to either a range of counts 0 to 10 or a range of counts 85 to 95, it may be determined that no particle P has passed by in front of the light receiving sensor 44.

Figure 4:
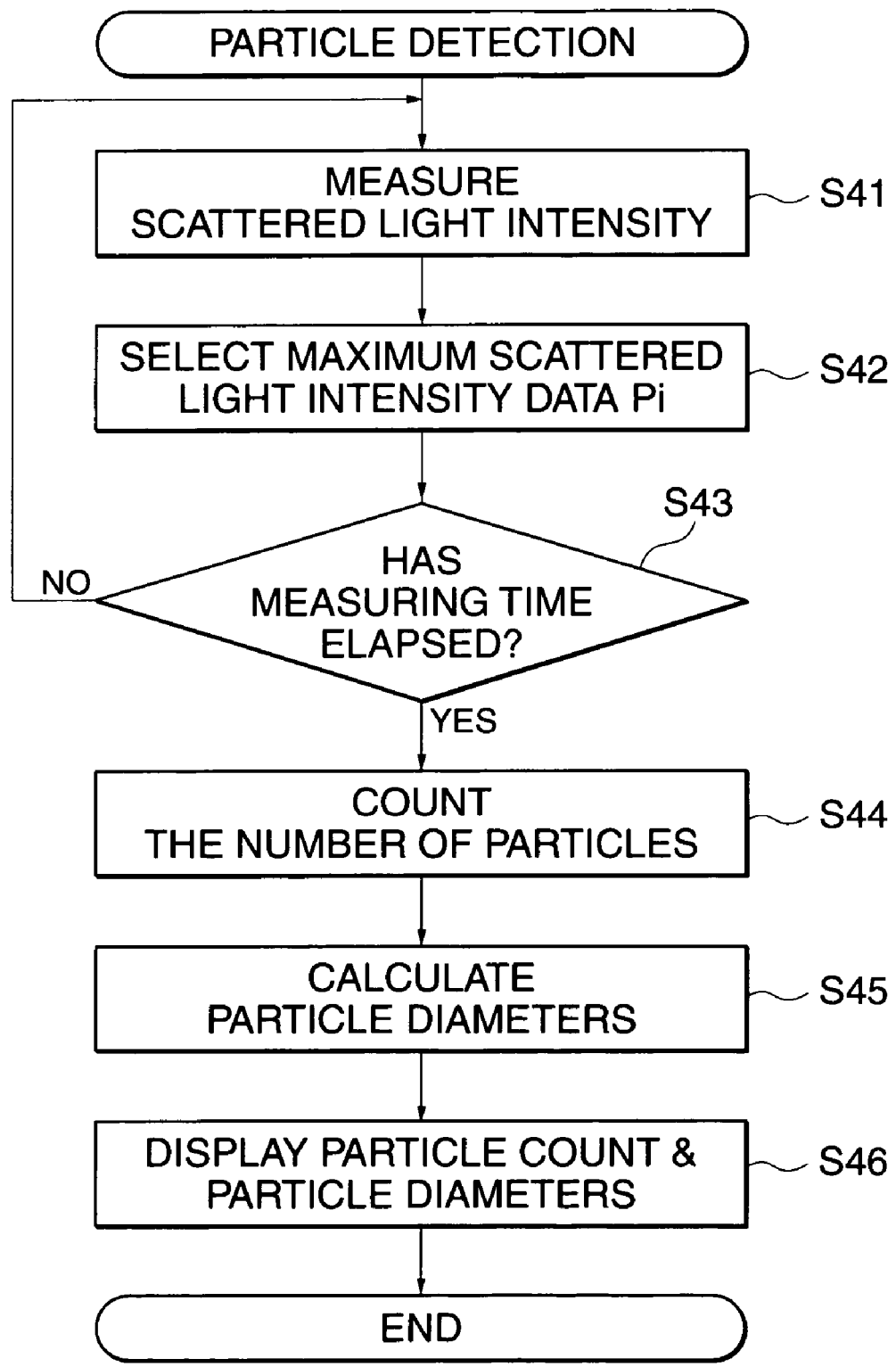
FIG. 4 is a flowchart showing a program for implementing the particle detecting method according to the present embodiment.

FIG. 4 is a flowchart showing a program for implementing the particle detecting method according to the present embodiment.

As shown in FIG. 4, first, the main evacuation line purges particles and the like from the chamber 10, and then the light receiving sensor 44 measures scattered light intensity at predetermined time intervals in respective measurement periods (step S41), and sends a measurement of scattered light intensity and time information associated with the measurement of scattered light intensity as scattered light intensity data to the particle counter 41. In this case, the light receiving sensor 44 does not measure scattered light intensity lower than the predetermined threshold value. This makes it possible to avoid measuring the intensity of light other than scattered light generated due to the presence of a particle P, i.e. the intensity of stray light or light generated e.g. due to fluctuation of plasma within the chamber 10.

Then, when the internal memory stores the scattered light intensity data obtained in a single measurement period, the maximum scattered light intensity-selecting section 46 selects maximum scattered light intensity data Pi from the stored scattered light intensity data (step S42), and the memory 47 stores the maximum scattered light intensity data Pi.

In the following step S43, it is determined whether or not the preset measuring time period has elapsed. If the measuring time period has not elapsed, the program returns to the step S41, whereas if the measuring time period has elapsed, the program proceeds to a step S44.

Then, if time information ti of the maximum scattered light intensity data Pi obtained in the measurement period corresponds to the count 0 or 95, it is determined that no particle P has passed by in front of the light receiving sensor 44 in the measurement period associated with the maximum scattered light intensity data Pi. On the other hand, if the time information ti does not correspond to either the count 0 or the count 95, it is determined that a single particle P has passed by in front of the light receiving sensor 44 in the measurement period associated with the maximum scattered light intensity data Pi. Thus, the number of particles P having passed by in front of the light receiving sensor 44 is counted (step S44), and the particle diameter of each particle P determined to have passed by in front of the light receiving sensor 44 is calculated based on scattered light intensity data Ii associated with time information ti for the particle P (step S45). More specifically, a particle diameter corresponding to the associated scattered light intensity data Ii is read out from a table prepared for showing the correlation between particle diameters and values of emitted light intensity. Thus, the size of each particle P having passed by in front of the light receiving sensor 44 can be calculated accurately.

Then, the particle detecting section 48 sends the count of particles P and the calculated particle diameter of each particle P to the display section 49, and the display section 49 displays the number of particles P and the particle diameter of each of the particles P (step S46), followed by terminating the program.

According to the above describe particle detecting method of the present embodiment, the number of particles P having passed by in front of the light receiving sensor 44 is counted based on the time information of the maximum scattered light intensity data obtained in the respective measurement periods instead of being counted based on only the values of maximum scattered light intensity obtained in the respective measurement periods. More specifically, in each measurement period, when time information of associated maximum scattered light intensity data corresponds to either the beginning or the end of the measurement period, it is determined that no particle P has passed by in front of the light receiving sensor 44, so that even the number of low-speed particles P each of which passes by in front of the light receiving sensor 44 over a plurality of measurement periods can be counted accurately.

Although in the above described embodiment, a description is given of the case where a single particle P passes by in front of the light receiving sensor 44 within a measuring time period, i.e. the case where superposition of scattered lights cannot occur, the particle detecting method according to the present embodiment can be applied to the case where a plurality of particles P pass by in front of the light receiving sensor 44 within a measuring time period, i.e. a case where scattered light beams are superposed one upon another.

Figure 5:
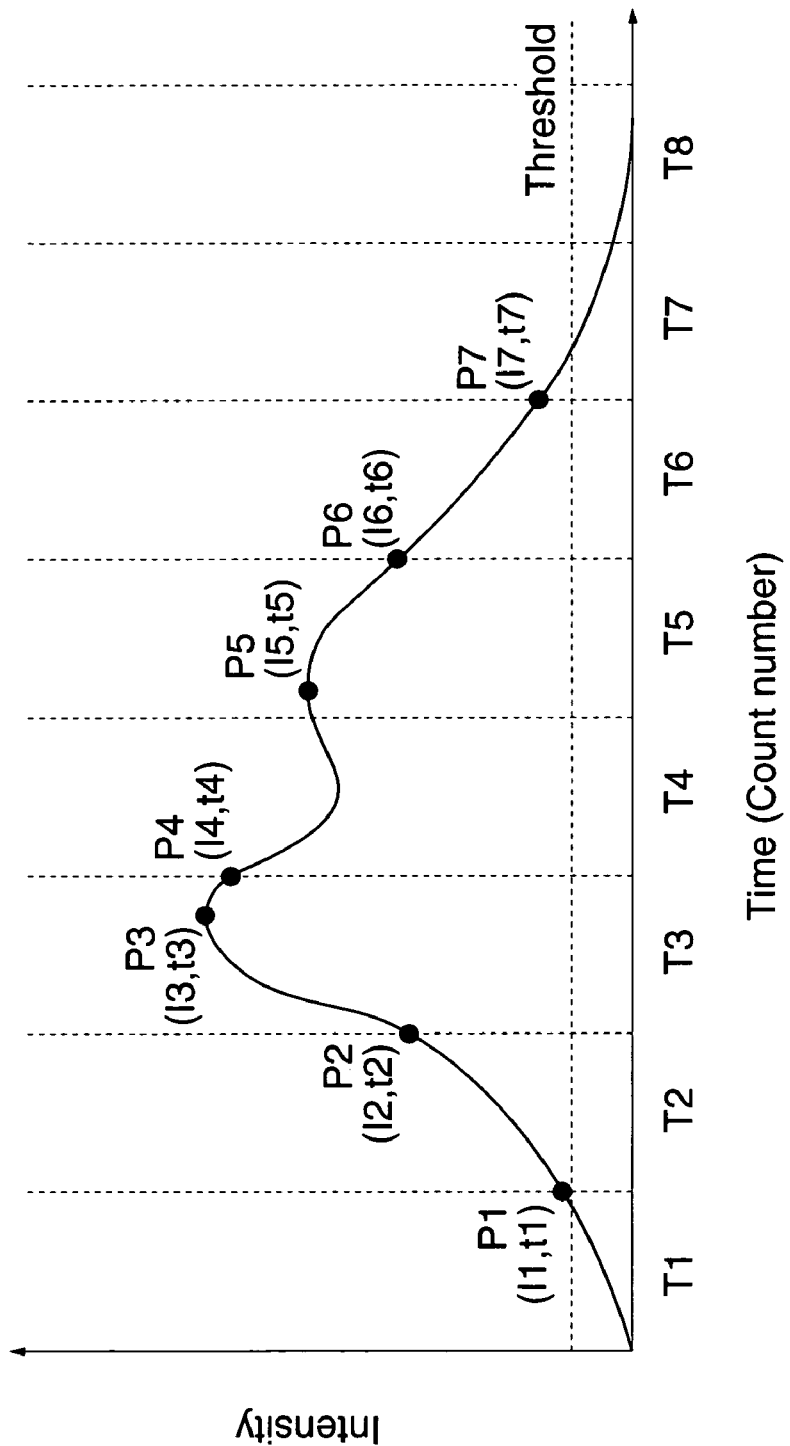
FIG. 5 is a graph showing changes with time in scattered light intensity in the case where scattered lights generated due to the presence of two particles are superposed one upon the other.

FIG. 5 is a graph showing changes with time in scattered light intensity in the case where scattered light beams generated due to presence of two particles P are superposed one upon the other. In FIG. 5, a relatively high-speed particle P passes by in front of the light receiving sensor 44 in a measurement period T3, and a relatively low-speed particle P passes by in front of the light receiving sensor 44 in a measurement period T5.

As shown in FIG. 5, when the particle detecting method according to the present embodiment is applied, since pieces of maximum scattered light intensity data P1 to P7 among maximum scattered light intensity data obtained in respective measurement periods Ti (i=1, 2, . . . , 8) each contain scattered light intensity Ii exceeding the predetermined threshold value, and pieces of time information t1 and t2 of the maximum scattered light intensity data P1 and P2 correspond to the respective ends of the measurement periods T1 and T2, it is determined that no particle P has passed by in front of the light receiving sensor 44 in either of the measurement periods T1 and T2. Further, pieces of time information t4, t6, and t7 of the respective maximum scattered light intensity data P4, P6, and P7 correspond to the respective beginnings of the measurement periods T4, T6, and T7, and therefore it is determined that no particle P has passed by in front of the light receiving sensor 44 in any of the measurement periods T4, T6, and T7. On the other hand, in each of the measurement periods T3 and T5 associated with the respective maximum scattered light intensity data P3 and P5, time information Ti does not correspond to either the beginning or the end of the associated measurement period, and therefore it is determined that a single particle P has passed by in front of the light receiving sensor 44. Consequently, it is determined that a total of two particles P have passed within the measuring time period.

As described above, according to the particle detecting method of the present embodiment, even when a plurality of particles P pass by in front of the light receiving sensor 44 within a measuring time period, it is possible to accurately detect the number of particles P having passed by in front of the light receiving sensor 44. In the above described embodiment, the scattered light intensity associated with the light flux L0 emitted into the purged gas stream in the evacuation pipe 50 of the main evacuation line is detected. In the substrate processing apparatus 2, particles P and the like within the chamber 10 are purged by the main evacuation line prior to decompression of the chamber 10. Therefore, the particles P can be easily detected.

The place for measuring scattered light intensity is not limited to the main evacuation line, but any place through which particles P are carried by a gas stream may be selected. For example, the substrate processing apparatus 2 may be provided with a roughing line comprised of another evacuation pipe for communicating between the space of the evacuation passage 12 downstream of the exhaust plate 13 and the DP 16, and a valve disposed in the evacuation pipe, and the intensity of scattered light generated in a purged gas stream flowing in the evacuation pipe may be measured by a particle monitor disposed in an intermediate portion of the evacuation pipe. In this case, particles P and the like within the chamber 10 are purged by the roughing line prior to decompression of the chamber 10. Therefore, particles P can be easily detected.

Further, the light flux L0 may be emitted into the chamber 10 through a window formed in the side wall of the chamber 10 so that scattered light intensity associated with the light flux L0 can be measured. Thus, the number of particles within the chamber 10, which cause degradation of the quality of semiconductor devices, can be directly detected, which makes it possible to reliably prevent degradation of the quality of the semiconductor devices.

Although the substrate processing apparatus to which is applied the particle detecting method according to the present embodiment is an etching apparatus, this is not limitative, but the substrate processing apparatus may be implemented by a coating/developing apparatus, a substrate cleaning apparatus, a heat treatment apparatus, a wet etching apparatus, or a film forming apparatus.

Further, the above described substrate processing apparatus may be provided with an operation control device that controls the operation of the substrate processing apparatus based on the particle diameters and the number of detected particles P. For example, the operation control device stops the operation of the substrate processing apparatus when the number of particles P with a particle diameter larger than a predetermined value exceeds a predetermined number. Thus, it is possible to prevent degradation of the quality of semiconductor devices.

Although in the above described embodiment, the particle detecting method is applied to a substrate processing apparatus, this is not limitative, but the method may be applied to detection of particles in a conveying chamber connected to the substrate processing apparatus, for carrying a semiconductor wafer W into and out of the substrate processing apparatus therethrough. In this case, it is preferred that scattered light intensity is detected in the conveying chamber or in an evacuation pipe connected to the conveying chamber.

Figure 6A:
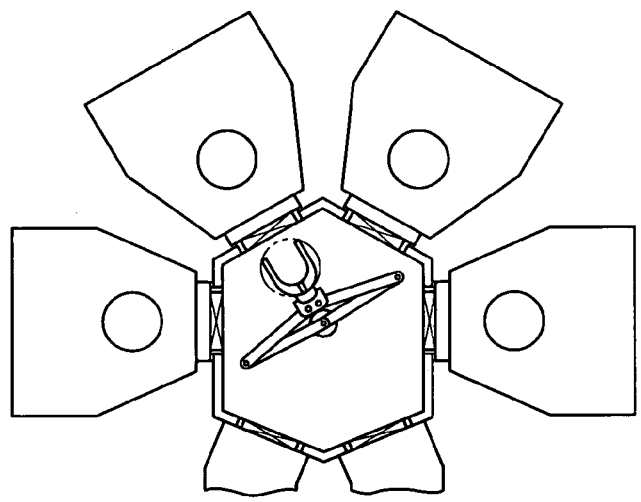
Figure 6B:
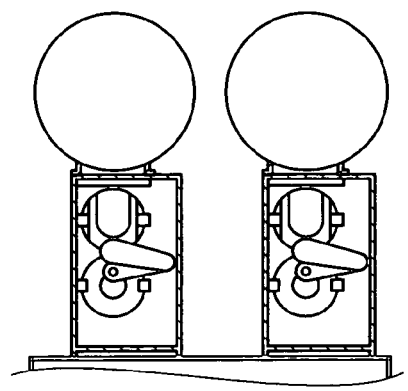
Figure 6C:
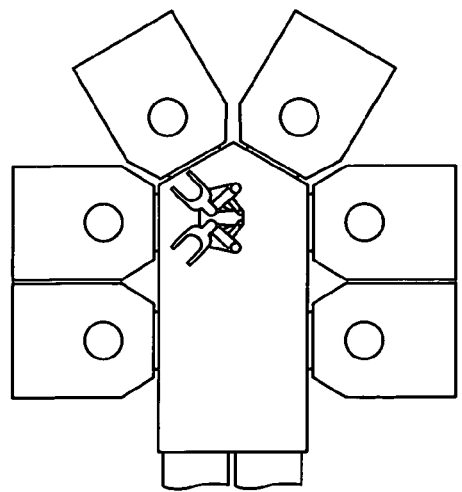
Figure 7:
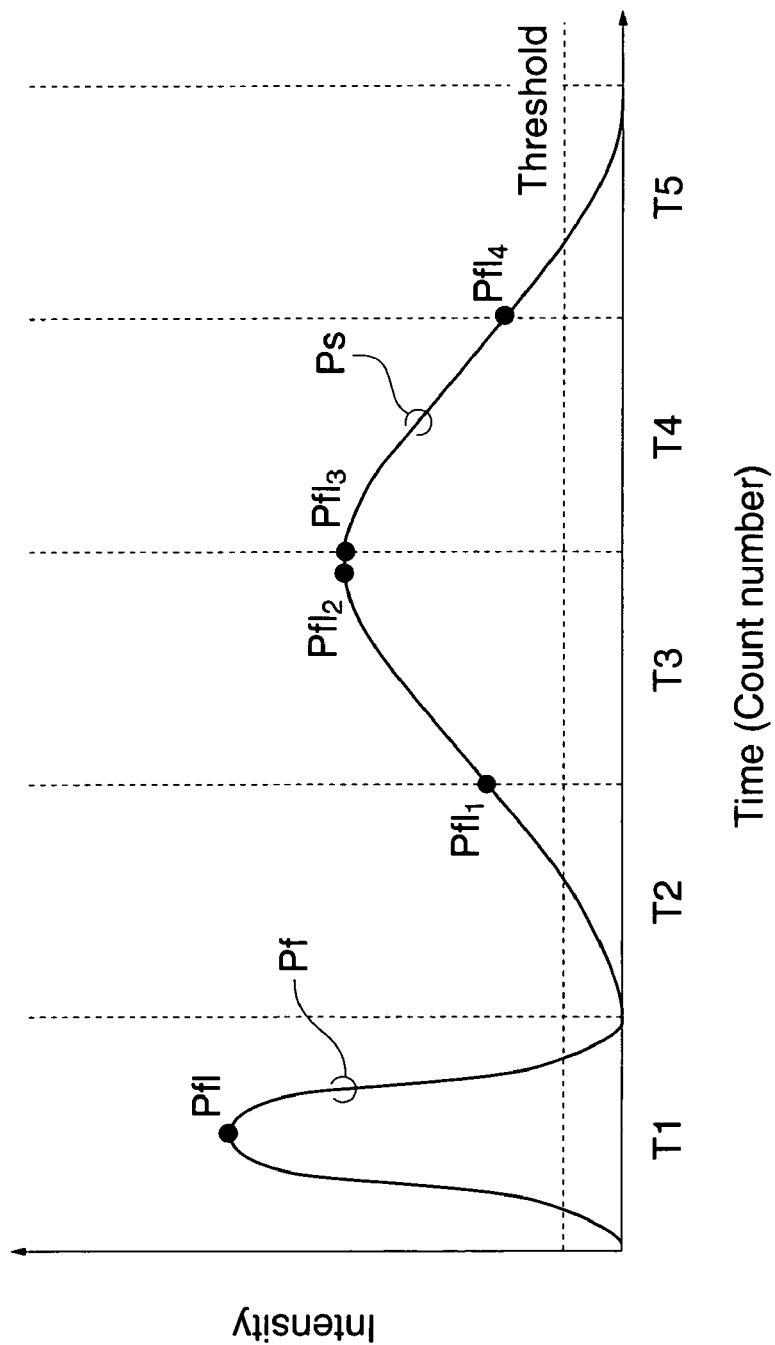
FIG. 7 is a graph showing changes with time in scattered light intensity detected by a conventional detection method.

As shown in FIGS. 6A to 6C, the substrate processing system including the substrate processing apparatus and the conveying chamber to which is applied the particle detecting method according to the present embodiment may be a cluster-type substrate processing system having a plurality of substrate processing apparatuses radially arranged around a conveying chamber provided with a frog leg-type transfer arm for conveying a semiconductor wafer W (see FIG. 6A), a parallel-type substrate processing system formed by two parallelly-disposed process ship each comprised of a substrate processing apparatus and a conveying chamber having a scalar-type transfer arm provided therein (see FIG. 6B), or a substrate processing system having a conveying chamber provided with a double arm-type transfer arm comprised of two scalar-type conveyor arms and a plurality of substrate processing apparatuses arranged in a manner surrounding the conveying chamber (see FIG. 6C).

Further, although in the above described embodiment, a substrate to be processed is a semiconductor wafer, this is not limitative, but a glass substrate e.g. for an LCD (Liquid Crystal Display) or an FPD (Flat Panel Display) may be processed, for example.

Further, it is to be understood that the object of the present invention may also be accomplished by supplying the particle counter 41 or an external server, such as an APC (Advance Process Control) server, with a storage medium in which a program code of software, which realizes the functions of the above described embodiment is stored, and causing the particle detecting section 48 of the particle counter 41 or a computer (or CPU or MPU) of the APC server to read out and execute the program code stored in the storage medium.

In this case, the program code itself read from the storage medium realizes the functions of the above described embodiment, and therefore the program code and the storage medium in which the program code is stored constitute the present invention.

Examples of the storage medium for supplying the program code include a floppy (registered trademark) disk, a hard disk, a magnetic-optical disk, an optical disk such as a CD-ROM, a CD-R, a CD-RW, a DVD-ROM, a DVD-RAM, a DVD-RW, and a DVD+RW, a magnetic tape, a nonvolatile memory card, and a ROM. Alternatively, the program may be downloaded via a network from another computer, a database, or the like, not shown, connected to the Internet, a commercial network, a local area network, or the like.

Further, it is to be understood that the functions of the above described embodiment may be accomplished not only by executing the program code read out by a computer, but also by causing an OS (operating system) or the like which operates on the computer to perform a part or all of the actual operations based on instructions of the program code.

Further, it is to be understood that the functions of the above described embodiment may be accomplished by writing a program code read out from the storage medium into a memory provided on an expansion board inserted into a computer or a memory provided in an expansion unit connected to the computer and then causing a CPU or the like provided in the expansion board or the expansion unit to perform a part or all of the actual operations based on instructions of the program code.

What is claimed is:

1. A particle detecting method of detecting particles carried by a gas stream, comprising:
   a scattered light intensity-measuring step of measuring intensity of scattered light generated when a light emitted into the gas stream is scattered by a particle, using a light receiving unit at predetermined time intervals;
   a maximum intensity measuring timing-selecting step of dividing a measuring time period for measuring the scattered light intensity into measurement periods each defined as a predetermined time period, and selecting a measured time point in each measurement period at which a maximum value of the scattered light intensity measured is measured; and
   a passed particle counting step of counting a number of particles having passed by in front of the light receiving unit, based on the measured time point selected in each measurement period.

2. A particle detecting method as claimed in claim 1, wherein said passed particle counting step determines that the particle has not passed by in front of the light receiving unit, when the measured time point selected in the measurement period corresponds to either a beginning or an end of the measurement period.

3. A particle detecting method as claimed in claim 1, wherein said scattered light intensity-measuring step does not measure scattered light intensity below a threshold value.

4. A particle detecting method as claimed in claim 1, wherein said maximum intensity measuring timing-selecting step selects not only the measured time point, but also the maximum value of scattered light intensity associated with the measured time point.

5. A particle detecting method as claimed in claim 1, further comprising a particle diameter calculating step of calculating particle diameters of the respective particles based on the maximum values of the scattered light intensity measured in the measurement periods.

6. A particle detecting method as claimed in claim 1, wherein said scattered light intensity-measuring step measures the scattered light intensity of the light emitted into the gas stream in a processing chamber provided in a substrate processing apparatus.

7. A particle detecting method as claimed in claim 1, wherein said scattered light intensity-measuring step measures the scattered light intensity of the light emitted into the gas stream in a purged gas flow path connected to a processing chamber provided in a substrate processing apparatus.

8. A computer-readable storage medium storing a particle detecting program for causing a computer to execute a particle detecting method of detecting particles carried by a gas stream, the program comprising:
   a scattered light intensity-measuring module for measuring intensity of scattered light generated when a light emitted into the gas stream is scattered by a particle, using a light receiving unit at predetermined time intervals;

a maximum intensity measuring timing-selecting module for dividing a measuring time period for measuring the scattered light intensity into measurement periods each defined as a predetermined time period, and selecting a measured time point in each measurement period at which a maximum value of the scattered light intensity measured is measured; and a passed particle counting module counting a number of particles having passed by in front of the light receiving unit, based on the measured time point selected in each measurement period.

* * * * *